(12) United States Patent
Summar et al.

(10) Patent No.: US 10,500,181 B2
(45) Date of Patent: *Dec. 10, 2019

(54) METHODS AND COMPOSITIONS FOR TREATMENT FOR CORONARY AND ARTERIAL ANEURYSMAL SUBARACHNOID HEMORRHAGE

(71) Applicant: Vanderbilt University, Nashville, TN (US)

(72) Inventors: Marshall L. Summar, Washington, DC (US); Frederick E. Barr, Little Rock, AR (US); Reid Carleton Thompson, Nashville, TN (US)

(73) Assignee: Vanderbilt University, Nashville, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/955,370

(22) Filed: Apr. 17, 2018

(65) Prior Publication Data

US 2018/0360787 A1 Dec. 20, 2018

Related U.S. Application Data

(60) Division of application No. 13/331,678, filed on Dec. 20, 2011, now Pat. No. 9,943,494, which is a continuation of application No. 12/322,434, filed on Feb. 2, 2009.

(60) Provisional application No. 61/025,170, filed on Jan. 31, 2008.

(51) Int. Cl.
    *A61K 31/198* (2006.01)

(52) U.S. Cl.
    CPC .................. *A61K 31/198* (2013.01)

(58) Field of Classification Search
    None
    See application file for complete search history.

(56) References Cited

U.S. PATENT DOCUMENTS

| | | | |
|---|---|---|---|
| 4,196,265 A | 4/1980 | Koprowski et al. |
| 4,458,066 A | 7/1984 | Caruther et al. |
| 4,554,101 A | 11/1985 | Hopp |
| 4,683,195 A | 7/1987 | Mullis et al. |
| 4,683,202 A | 7/1987 | Mullis |
| 4,736,866 A | 4/1988 | Leder et al. |
| 4,769,331 A | 9/1988 | Roizman et al. |
| 4,965,188 A | 10/1990 | Mullis et al. |
| 4,996,236 A | 2/1991 | Nakamura et al. |
| 5,162,215 A | 11/1992 | Bosselman et al. |
| 5,217,997 A | 6/1993 | Levere |
| 5,279,833 A | 1/1994 | Rose |
| 5,286,634 A | 2/1994 | Stadler et al. |
| 5,286,739 A | 2/1994 | Kilbourn et al. |
| 5,334,380 A | 8/1994 | Kilbourn et al. |
| 5,374,651 A | 12/1994 | Kilbourn et al. |
| 5,385,940 A | 1/1995 | Moskowitz |
| 5,399,346 A | 3/1995 | Anderson et al. |
| 5,489,742 A | 2/1996 | Hammer et al. |
| 5,550,024 A | 8/1996 | Rothschild |
| 5,550,316 A | 8/1996 | Mintz |
| 5,573,933 A | 11/1996 | Seamark et al. |
| 5,614,396 A | 3/1997 | Bradley et al. |
| 5,625,125 A | 4/1997 | Bennett et al. |
| 5,641,484 A | 6/1997 | Hung et al. |
| 5,643,567 A | 7/1997 | Hung et al. |
| 5,646,008 A | 7/1997 | Thompson et al. |
| 5,648,061 A | 7/1997 | Bernstein et al. |
| 5,651,964 A | 7/1997 | Hung et al. |
| 5,741,957 A | 4/1998 | Deboer et al. |
| 5,767,160 A * | 6/1998 | Kaesemeyer ........ A61K 31/195 514/565 |
| 5,873,359 A | 2/1999 | Zapol et al. |
| 5,874,471 A | 2/1999 | Waugh |
| 5,891,459 A | 4/1999 | Cooke et al. |
| 6,028,107 A | 2/2000 | Waugh |
| 6,331,543 B1 | 12/2001 | Garvey et al. |
| 6,337,321 B1 | 1/2002 | Cooke et al. |
| 6,343,382 B2 | 2/2002 | Sciglia |
| 6,346,382 B1 | 2/2002 | Summar et al. |
| 6,358,536 B1 | 3/2002 | Thomas |
| 6,642,208 B2 | 11/2003 | Cooke et al. |
| 6,646,006 B2 | 11/2003 | Cooke et al. |
| 6,689,810 B2 | 2/2004 | Martin |

(Continued)

FOREIGN PATENT DOCUMENTS

| AU | 3460571 A | 4/1973 |
| CN | 1946388 A | 4/2007 |

(Continued)

OTHER PUBLICATIONS

Abman et al., "Role of endothelium-derived relaxing factor during transition of the pulmonary circulation at birth," Am. J. Physiol., vol. 259, pp. H1921-H1927 (1990).

Abman, S. H.; Arch Dis Child Fetal Neonatal Ed (2002) 87: F15-F18.

Adelman et al., "In Vitro Deletional Mutagenesis for Bacterial Production of the 20,000-Dalton Form of Human Pituitary Growth Hormone," DNA, vol. 2, p. 183-193 (1983).

Advisory Action corresponding to U.S. Appl. No. 12/364,078 dated May 23, 2011.

Ahrens et al., "Consensus statement from a Conference for the Management of Patients With Urea Cycle Disorders," Supplement to the Journal of Pediatrics, vol. 138, No. 1, pp. S1-S5 (Jan. 2001).

(Continued)

*Primary Examiner* — Svetlana M Ivanova
(74) *Attorney, Agent, or Firm* — Hunton Andrews Kurth LLP

(57) ABSTRACT

Methods and compositions for treating a complication associated with aneurysmal subarachnoid hemorrhage (SAH), the method comprising administering an effective amount of a nitric oxide precursor to a subject in need thereof. Methods and compositions for treating vasospasm, the method comprising administering an effective amount of a nitric oxide precursor to a subject in need thereof.

6 Claims, 1 Drawing Sheet

(56) References Cited

U.S. PATENT DOCUMENTS

| | | | |
|---|---|---|---|
| 6,743,823 | B1 | 6/2004 | Summar et al. |
| 8,188,147 | B2 | 5/2012 | Summar et al. |
| 9,943,494 | B2* | 4/2018 | Summar ............ A61K 31/198 |
| 2001/0056068 | A1 | 12/2001 | Chwalisz et al. |
| 2002/0013288 | A1 | 1/2002 | Cooke et al. |
| 2003/0026849 | A1 | 2/2003 | Thomas |
| 2003/0134332 | A1 | 7/2003 | Boykin, Jr. |
| 2004/0025953 | A1 | 11/2004 | Summar et al. |
| 2004/0235953 | A1* | 11/2004 | Summar ............ A61K 31/195 514/565 |
| 2006/0194728 | A1 | 8/2006 | Killian et al. |
| 2007/0026448 | A1 | 2/2007 | Ramanathan et al. |
| 2007/0184554 | A1 | 8/2007 | Teuscher et al. |
| 2008/0234379 | A1 | 9/2008 | Summar et al. |
| 2009/0197964 | A1 | 8/2009 | Summar et al. |
| 2009/0312423 | A1 | 12/2009 | Summar et al. |

FOREIGN PATENT DOCUMENTS

| | | | |
|---|---|---|---|
| CN | ZL200580012693.5 | 3/2012 | |
| EP | 044119 | A2 | 8/1991 |
| GB | 2322551 | | 9/1998 |
| WO | 1994/16740 | A | 8/1994 |
| WO | 99/18949 | A1 | 4/1999 |
| WO | WO-9918949 | A1 * | 4/1999 ............ A61K 31/00 |
| WO | 00/06151 | | 2/2000 |
| WO | 2000/73322 | A | 12/2000 |
| WO | 2001/056068 | A1 | 12/2001 |
| WO | 2005/082042 | | 9/2005 |

OTHER PUBLICATIONS

Akashi et al. "Citrulline, a novel compatible solute in drought-tolerant wild watermelon leaves, is an efficient hydroxyl radical scavenger," FEBS Lett., vol. 508, No. 3, pp. 438-442 (Nov. 23 2001). (Abstract).
Akisu et al., "Protective Effect of Dietary Supplementation with L-Arginine and L-Carnitine on Hypoxia/Reoxygenation Induced Necrotising Enterocolitis in Young Mice," Biology of the Neonate, vol. 81, pp. 260-265 (2002). (Abstract).
Allen, J. and ATS subcommittee AoP, Am J Respir Crit Care Med (2003) 168: 356-396.
Alonso et al., "Affinity Cleavage of Carbomoyl-Phosphate Synthetase I Localizes Regions of the Enzyme Interacting with the Molecule of ATP that Phosphyorylates Carbamate," Eur. J. Biochem., pp. 377-384, (1995).
Alves et al. "The SGOT/SGPT rataio in alcoholic liver disease," Acta Med. Port., vol. 3, No. 4, pp. 255-260 (Jul.- Aug. 1981). (Abstract).
American Lung Association (2016) Bronchopulmonary Dsyplasia (12 pages).
American Lung Association (2016) Diagnosing and Treating Bronchopulmonary Dysplasia (12 pages).
American Lung Association (2016) Learn about Bronchopulmonary Dysplasia (19 pages).
Amin, et al. (2002) "Arginine supplementation prevents necrotizing enterocolitis in the premature infant." Journal of Pediatrics 140(4): 425-431.
Ananthakrishnan et al., "L-Citrulline ameliorates chronic hypoxia-induced pulmonary hypertension in newborn piglets," Am. J. Physiol. Lung Cell. Mol. Physiol., vol. 297, pp. L506-L511 (2009).
Anggard (1994) Lancet 343(8907): 1199-1206.
Artymiuk et al., "Biotin carboxylase comes into the fold," Nature Struct. Biol., vol. 3, pp. 128-132 (1996).
Aschner (2004) Pediatric Pulmonology 26: 132-135.
Aschner, Chief of Neonatology and Professor of Pediatrics M.D., University of Rochester, 1981, (Medicine).
Aschner, J. L., "New Therapies for Pulmonary Hypertension in Neonates and Children," Pediatr. Pulmonol. Suppl., vol. 26, pp. 132-135 (2004).

Asthma, The Merck Manual of Diagnosis and Therapy, 17th Ed. (1999), pp. 556-557, Merck Research Laboratories, Whitehouse Station, NJ.
AU 2009203177 (Jan. 31, 2012), Examination Rpt, , 3 pgs.
Australian Patent Office Examination Report dated Nov. 2, 2007 for Australian Patent Application No. 2005216270.
Awrich, et al. (1975) "Hyperdibasicaminoaciduria, hyperammonemia, and growth retardation." Journal of Pediatrics 87(5): 731-738.
Bachmann et al., New England Journal of Medicine, vol. 304, p. 543 (1981).
Balasubramaniam et al. (2006), Am J Physiol Lung Cell Mol Physiol, 291(1):L119-L127.
Ballard et al., "Inhaled nitric oxide in preterm infants undergoing mechanical ventilation," N. Engl. J. Med., vol. 355, No. 4, pp. 343-353 (2006).
Barr (Aug. 2007) J of Thoracic and Cardiovascular Surgery 134(2):319-326.
Barr et al., "Effect of cardiopulmonary bypass on urea cycle intermediates and nitric oxide levels after congenital heart surgery," The Journal of Pediatrics, vol. 142, No. 1, pp. 26-30 (2003).
Barsotti, "Measurement of ammonia in blood," The Journal of Pediatrics, vol. 138, pp. S11-S20 (Jan. 2001).
Batista da Costa, Jr. et al., "Surgical treatment of intracranial aneurysms: six-year experience in Belo Horizonte, MG, Brazil," Arq Neuro-Psiquiatr (Sao Paulo), vol. 62, pp. 245-249 (2004).
Batshaw and Brusilow, "Valproate-induced hyperammonemia," Annals of Neurology, vol. 11, No. 3, pp. 319-321 (1982).
Batshaw et al., "Alternative pathway therapy for urea cycle disorders: Twenty years later," J. Pediatr., vol. 138, pp. S46-S55 (2001).
Baudouin, et al. (1993) "L-arginine infusion has no effect on systemic haemodynamics in normal volunteers, or systemic and pulmonary haemodynamics in patients with elevated pulmonary vascular resistance." British Journal of Clinical Pharmacology 36(1): 45-49.
Baumgartner et al. "Hyperammonemia with reduced ornithine, arginine and praline: a new inborn error caused by a mutation in the gene encoding delta(1)-pyrroline-5-carboxylate synthase," Hum. Mol. Genet., vol. 9, No. 19, pp. 2853-2858 (Nov. 22, 2000).
Bearman, S.I., "Venoocclusive disease of the liver: Development of a model for predicting fatal outcome after marrow transplantation," Journal of Clinical Oncology, vol. 11, pp. 1729-1736 (1993).
Beaucage et al., "Deoxynucleoside phosphoramidites—a new class of key intermediates for deoxypolynucleotide synthesis," Tetrahedron Letters, vol. 22, pp. 1859-1862 (1981).
Beaumier, L., "Arginine: New and exciting developments for an 'old' amino acid," Biomedical & Environmental Sciences, vol. 9, pp. 296-315 (1996).
Becker et al., Archives of Biochemistry & Biophysics, vol. 223, pp. 381-392 (1983).
Benedetto et al., "Increased L-citrulline/L-arginine plasma ratio in severe preclampsia," Obstet Gynecol, vol. 96, No. 3, pp. 395-399 (Sep. 2000). (Abstract).
Berkenbosch et al., "Decreased synthesis and vasodilation to nitric oxide in piglets with hypoxia-induced pulmonary hypertension," Am. J. Physiol. Jung Cell. Mol. Physiol., vol. 278, pp. L276-L283 (2000).
Bernard et al, Intensive Care Medicine, vol. 20, pp. 225-232 (1994).
Bernasconi et al. (2002) Pediatr Cardiol 4(1): 4-29.
BIOSIS Database Accession No. PREV199699075415 [on-line] Biosciences Information service, Philadelphia, PA, US; 1996.
BIOSIS Database Accession No. PREV199799686392 [on-line] Biosciences Information service, Philadelphia, PA, US; 1997.
BIOSIS Database Accession No. PREV199800177848 [on-line] Biosciences Information service, Philadelphia, PA, US; Feb. 1998.
BIOSIS Database Accession No. PREV200200378590 [on-line] Biosciences Information service, Philadelphia, PA, US; May 2002.
BIOSIS Database Accession No. PREV200400055833 [on-line] Biosciences Information service, Philadelphia, PA, US; Dec. 2003.
Blau, et al. (1996) Physician's Guide to the laboratory Diagnosis of Metabolic Diseases, London, Chapman & Hall Medical [Table of Contents].

(56) References Cited

OTHER PUBLICATIONS

Blum et al., "Oral L-arginine in Patients with Coronary Artery Disease on Medical Management," Circulation, vol. 101, pp. 2160-2164 (May 9, 2000).
Boeger, et al. (1996) "Differential systemic and pulmonary hemodynamic effects of L-arginine in patients with coronary artery disease or primary pulmonary hypertension." International Journal of Clinical Pharmacology and Therapeutics 34(8): 323-328.
Boger et al. "Is asymmetric dimethylarginine a novel mark of atherosclerosis?" Circulation, vol. 101, No. 14, pp. 160-161 (Apr. 11, 2000). (Abstract).
Boger et al., "An endogenous inhibitor of nitric oxide synthase regulates endothelial adhesiveness for monocytes," J. Am. Cardiol., vol. 36, No. 7, pp. 2287-2295 (Dec. 2000).
Boger, R. H., Curr Opin Clin Nutr and Met Care (2008) 11:55-61.
Bourbon et al. (2005), Pediatric Res, 57:38R-46R.
Bourrier et al., Prese Medicale, vol. 17, pp. 2063-2066 (1988).
Bredt, "Endogenous nitric oxide synthesis: biological functions and pathophysiology," Free Radic. Res., vol. 31, No. 6, pp. 577-596 (Dec. 1999). (Abstract).
Bronchopulmonary Dysplasia—PubMed Health website A.D.A.M. Medical Encyclopedia (2011) [Nov. 30, 2012] (3 pages).
Bruno et al. "Population pharmacokinetics and pharmacokinetic-pharmacodynamic relationships for docetaxel," Invest. New Drugs, vol. 19, No. 2, pp. 163-169 (May 2001). (Abstract).
Caroline et al., "Acute L-arginine supplement and cardiac surgery," Canadian J. Anesth., vol. 43, p. _A16 (1996).
Castillo et al., "Whole body arginine metabolism and nitric oxide synthesis in newborns with persistent pulmonary hypertension," Pediatr. Res., vol. 38, pp. 17-24 (1995).
Castro-Gago et al., Child Neuro Systems, vol. 6, pp. 434-436 (1990).
Cervera et al., "Photoaffinity labeling with UMP of lysine 992 of carbamyl phosphate synthetase from *Escherichia coli* allows identification of the binding site for the pyrimidine inhibitor," Biochemistry, vol. 35, pp. 7247-7255 (1996).
Chan et al., "Asymmetric dimethylarginine increases mononuclear cell adhesiveness in hypercholesterolemic humans," Arterioscler. Thromb. Vasc. Biol., vol. 20, No. 4, pp. 1040-1046 (Apr. 2000). (Abstract).
Cheung et al., "Channeling of Urea Cycle Intermediates in Situ in Permeabilized Hepatocytes," J. Biol. Chem., vol. 264,,pp. 4038-4044 (1989).
Chin-Dusting et al., "Dietary supplementation with L-arginine fails to restore endothelial function in forearm resistance arteries of patients with severe heart failure," J. Am. Coll. Cardiol., vol. 27, pp. 1207-1213 (1996).
Chwalisz et al., "Role of nitric oxide in implantation and menstruation," Hum. Reprod., vol. 15, Suppl. 3, pp. 96-111 (Aug. 2000). (Abstract).
CN 200980109150.3 (Jul. 3, 2012), Office Action.
Cohen et al., "The SGOT/SGPT ratio—an indicator of alcoholic liver disease," Dig. Dis. Sci., vol. 24, No. 11, pp. 835-838 (Nov. 1979). (Abstract).
Cohen P. P., Current Topics in Cellular Regulation, vol. 18, pp. 1-19 (1981).
Communication pursuant to Article 94(3) EPC corresponding to European Patent Application No. 05 723 789.3-2123 dated Aug. 4, 2008.
Communication pursuant to Article 96(2) EPC corresponding to European Application No. 05 723 789.3-2123 dated Sep. 14, 2007. Resubmit.
Conner et al., Proc. Natl. Acad. Sci. U.S.A. 80:278(1983).
Cooke et al., "Atherogenesis and the arginine hypothesis," Curr. Atheroscler. Rep., vol. 3, No. 3, pp. 252-259 (May 2001). (Abstract).
Cooke, "Does ADMA cause endothelial dysfunction?" Arterioscler. Thromb. Vasc. Biol., vol. 20, No. 9, pp. 2032-2037 (Sep. 2000). (Abstact).
Cooke, "The endothelium: a new target for therapy," Vasc. Med., vol. 5, No. 1, pp. 49-53 (2000). (Abstract).
Coude et al., "Inhibition of ureagenesis by valproate in rat hepatocytes. Role of N-acetylglutamate and acetyl-CoA," Biochem. J., vol. 216, pp. 233-236 (1983).
Coude et al., J. Clin. Invest., vol. 64, pp. 1544-1551 (1979).
Coulter et al., Lancet, vol. 1, No. 8181, pp. 1310-1311 (1980).
Crea et al., Proc. Natl. Acad. Sci. USA, vol. 75, pp. 5765-5769 (1978).
Davies et al., "Idiopathic hyperammonemia: a frequently lethal complication of bone marrow transplantation", Bone Marrow Transplantation, vol. 17, pp. 1119-1125 (Jun. 1996).
de Groot et al., Biochemical & Biophysical Research Communications, vol. 124, pp. 882-888 (1984).
Dikalova et al. (Jan. 2014), PLOS One, 9(1):e85730.
Dimopoulou et al., "High Incidence of Neuroendocrine Dysfunction in Long-Term Survivors of Aneurysmal Subarachnoid Hemorrhage," Stroke, vol. 35, pp. 2884-2889 (2004).
Dioguardi (2011) J Nutrigenet Nutrigenomics 4: 90-98.
Dmitriev, "Optimal", Russian Language Dictionary, 2 pages (w/trans).
Dulak et al. "Nitric oxide induces the synthesis of vascular endothelial growth factor by rat vascular smooth muscle cells," Arterioscler. Thromb. Vasc., vol. 20, No. 3, pp. 659-666 (Mar. 2000). (Abstract).
Durand et al., "Acute liver failure in infancy: a 14-year experience of a pediatric liver transplantation center," J. Pediatr., 139(6): 871-876 (Dec. 2000). (Abstract).
Eadie et al., "Valproate-associated hepatotoxicity and its biochemical mechanisms," Med. Toxicol., vol. 3, pp. 85-106 (1998).
Eichenlaub et al., "Mutants of the mini-F plasmid pML31 thermosensitive in replication," J. Bacteriol., vol. 138, pp. 559-566 (1979).
EMBASE Database Accession No. EMB-1990075119 [on-line] Elsevier Science Publishers, Amsterdam, NL; 1990.
EMBASE Database Accession No. EMB-2003218186 [on-line] Elsevier Science Publishers, Amsterdam, NL; May 27, 2003.
EP 05723789.3 (Mar. 13, 2007), Search Report, 8 pgs.
Erez, et al. (2011) Nature Medicine 17(12): 1619-1626.
Erlich et al., Science, vol. 252, pp. 1143-1151 (Jun. 1991).
Escobedo et al. (1982), Experimental and Mol Pathology, 37:323-334.
European Search Report corresponding to European Patent Application No. 10184493 dated Mar. 30, 2011.
European Search Report corresponding to European Patent Application No. 09707788.7-2123/2247297 dated Apr. 28, 2011.
Examiner's Report corresponding to Australian Patent Application No. 2009203177 dated Jun. 8, 2010.
Faber-Langendoen et al., Bone Marrow Transplantation, vol. 12, pp. 501-507 (1993).
Fagan et al., "L-arginine reduces 1-10 right heart hypertrophy in hypoxia-induced pulmonary hypertension", Biochemical and Biophysical Research Communications, vol. 254, No. 1, pp. 100-103, (Jan. 8, 1999).
Fearon et al., "Genetic Analysis of Carbamyl Phosphate Synthetase I Deficiency," Human Genetics, vol. 70, No. 3, pp. 207-210 (1985).
Feng et al., "Effects of L-arginine on endothelial and cardiac function in rats with heart failure," Eur. J. Pharmacol., vol. 376, pp. 37-44 (Jul. 2, 1999).
Fike et al. (2014), Acta Paediatr, 8 pgs.
Fike, C. D. et al., J Appl Physiol (2000) 88:1797-1803.
Fike, C. D., et al., American Journal of Physiology (Lung, Cellular and Molecular Physiology 18) (1998) 274: L517-L526.
Fike, et al. (2000) Journal of Applied Physiology 88(5): 1797-1803.
Finckh et al., Human Mutation, (1998) vol. 12, No. 3, pp. 206-211.
First Office Action for CN200980109147.1—Sep. 5, 2012(10 pages).
Flett et al., "Aneurysmal Subarachnoid Hemorrhage: Management Strategies and Clinical Outcomes in a Regional Neuroscience Center," AJNR Am. J. Neuroradiol., vol. 26, pp. 367-372 (2005).
Gardiner, et al. (1995) Crit Care Med, 23(7):1227-1232.
Gebhardt et al., "Treatment of Cirrhotic Rats with L-Ornithine-L-Aspartate Enhances Urea Synthesis and Lowers Serum Ammonia Levels," The Journal of Pharmacology and Experimental Therapeutics, vol. 283, No. 1, pp. 1-6 (1997).
Genbank Accession No. AB005063.
Genbank Accession No. AH005315.
Genbank Accession No. BAA21088.
Genbank Accession No. M11710.

(56) References Cited

OTHER PUBLICATIONS

Genbank Accession No. M12318.
Genbank Accession No. M12319.
Genbank Accession No. M12320.
Genbank Accession No. M12321.
Genbank Accession No. M12322.
Genbank Accession No. M12323.
Genbank Accession No. M12324.
Genbank Accession No. M12325.
Genbank Accession No. M12326.
Genbank Accession No. M12327.
Genbank Accession No. M12328.
Genbank Accession No. M12335.
Genbank Accession No. M27174.
Genbank Accession No. P03965.
Genbank Accession No. P07258.
Genbank Accession No. X67573.
Genetics Home Reference "Lysinuric protein intolerance." (2011) [4 pages].
Ghishan et al., "Polymerase Chain Reaction (PCR) Detectable Polymorphisms in the Prenatal Diagnosis of Carbamyl Phosphate Synthetase I Deficiency," Gastroenterology, vol. 106, No. 4, Suppl., p. A1028 (1994).
Goodman et al. (Jan. 1988), J Pedi, 112(1):67-72.
Gribskov et al., "Sigma factors from *E. coli*, B. subtilis, phage SP01, and phage T4 are homologous proteins," Nucl. Acids. Res., vol. 14, pp. 6745-6763 (1986).
Grover et al. Am J Physiol Lung Cell Mol Physiol (2005) 288: L648-L654.
Guillou et al., "*Escherichia coli* Carbamoyl-Phosphate Synthetase: Domains of Glutaminase and Synthetase Subunit Interaction," Proc. Natl. Acad. Sci. USA, pp. 8304-8308 (Nov. 14, 1989).
Guy et al., "Determination of hepatic zinc content in chronic liver disease due to hepatitis By virus," Hepatogastroenterology, vol. 45, No. 20, pp. 472-476 (Mar.-Apr. 1998). (Abstract).
Guy et al., "Substructure of the Amidotransferase Domain of Mammalian Carbamyl Phosphate Synthetase," J. Biol. Chem., vol. 270, No. 5, pp. 2190-2197 (Feb. 3, 1995).
Haraguchi et al., "Cloning and Sequence of a CDNA Encoding Human Carbamyl Phosphate Synthetase I Molecular Analysis of Hyperammonemia," Gene, vol. 107, No. 2, pp. 335-340 (1991).
Harlow & Lane, (1988) Antibodies A Laboratory Manual, Cold Spring Harbor Laboratory [Table of Contents].
Harrison 1997, J. Clin. Invest., 100: 2153-2157.
Hauser et al., "Allopurinol-induced orotidinuria," New England Journal of Medicine, vol. 322, pp. 1641-1645 (1990).
Hebert, P.C., "A simple multiple system organ failure scoring system predicts mortality of patients who have sepsis syndrome," Chest, vol. 104, pp. 230-235 (1993).
Hecker, et al. 1990, Proc. Nat. Acad. Sci., 87: 8612-8616.
Hess "Use of Inhaled Nitric Oxide in the Hypoxic Newborn" (2005).
Hladunewich et al., "Effect of L-arginine therapy on the glomerular injury of preeclampsia: a randomized controlled trial," Obstet. Gynecol., vol. 107, pp. 886-895 (2006).
Hojo, et al. 1990, Cancer j, 3(1):14-19.
Horiuchi et al., "Sex-Related Differences in Patients Treated Surgically for Aneurysmal Subarachnoid Hemorrhage," Neurol. Med. Chir. (Tokyo), vol. 46, pp. 328-332 (2006).
Hoshide et al., J. Clin. Invest., vol. 91(5), pp. 1884-1887 (May 1993).
Hypertension, Pub Med Health, A service of the National Library of Medicine, National Institutes of Health, A.D.A.M. Medical Encyclopedia, Atlanta, GA, 2011.
Ikeda et al., "Cardiovascular effects of citrullinr in ischemia/ reperfusion injury via a non-nitric oxide-mediated mechanism," Methods Find. Exp. Clin. Pharmacol., vol. 22, No. 7, pp. 563-571 (Sep. 2000). (Abstract).

International Search Report and Written Opinion corresponding to PCT international application No. PCT/US05/06081 dated Dec. 23, 2005.
Interview Summary corresponding to U.S. Appl. No. 10/785,374 dated Jun. 1, 2009.
Interview Summary corresponding to U.S. Appl. No. 09/585,077 dated Nov. 4, 2004.
Suarez et al., "Aneurysmal Subarachnoid Hemorrhage," N. Engl. J. Med., vol. 354, pp. 387-396 (2006).
Jang et al., "Angiogenesis is impaired by hypercholesterolemia: role of asymmetric dimethylarginine," Circulation, vol. 102, No. 12, pp. 1414-1419 (Sep. 19, 2000). (Abstract).
Javid-Majd et al., "Comparison of the Functional Differences for the Homologous Residues within the Carboxy Phosphate and Carbamate Domains of Carbamoyl Phosphate Synthetase," Biochemistry, vol. 35, pp. 14362-14369 (1996).
Jobe et al., "Bronchopulmonary Dysplasia," Am. J. Respir. Crit. Care Med., vol. 163, pp. 1723-1729 (2001).
Notice of Allowance corresponding to U.S. Appl. No. 09/323,472 (U.S. Pat. No. 6,346,382) dated Aug. 9, 2001.
JP 2006-554329 (Sep. 13, 2011), Office Action, pp. 8.
Jung et al. J Neurosurg (2004) 101: 836-842.
Kamoun et al., "Valproate-induced inhibition of urea synthesis," Lancet, vol. 1, p. 48 (1987).
McCaffrey et al., "Effect of L-Arginine Infusion on Infants with Persistent Pulmonary Hypertension of the Newborn," Biol. Neonate, vol. 67, No. 4, pp. 240-243 (1995).
Kinsella et al. (2014), J Pediatr, 6 pgs.
Kinsella et al., "Bronchopulmonary dysplasia", Lancet, vol. 367, No. 9520, pp. 1421-1431 (Apr. 29, 2006).
Kinsella et al., "Low-dose inhalational nitric oxide in persistent pulmonary hypertension of the newborn," Lancet, vol. 340, pp. 819-820 (1992).
Kivisaari et al., "MR Imaging After Aneurysmal Subarachnoid Hemorrhage and Surgery: A Long-term Follow-up Study," AJNR Am. J. Neuroradiol., vol. 22, pp. 1143-1148 (Jun./Jul. 2001).
Kuhn et al. Circulation (2002) vol. 106, No. 19, Supplement pll 330 Abstract 1692.
Kurowska, "Nitric oxide therapies in vascular diseases," Curr. Pharm. Des., vol. 8, No. 3, pp. 155-166 (2002). (Abstract).
Kyte & Doolittle, "A simple method for displaying the hydropathic character of a protein," J. Mol. Biol., vol. 157, pp. 105-132 (1982).
Ladha et al. Am J Respir Cirt Care Med (2005) 172(6): 750-756.
Lagace et al., "Rat Carbamyl-Phosphate Synthetase I Gene," J. Biol. Chem, vol. 262, No. 22, pp. 10415-10418 (Aug. 5, 1987).
Landgren et al., Science, 241:1007, (1988).
Landgren et al., Science, 242:229-237, (1988).
Lassala et al. (2009), J Nutri 139:660.
Laursen et al., "Hypoxia-induced pulmonary vascular remodeling and right ventricular hypertrophy is unaltered by long-term oral L-arginine administration," Vascul. Pharmacol., vol. 49, pp. 71-76 (2008).
Lee et al. (1996) JPET, 276:353-358.
Leonard, J., "The nutritional management of urea cycle disorders," The Journal of Pediatrics, vol. 138, No. 1, pp. S40-S45 (2001).
Lipsitz et al., "Endogenous nitric oxide and pulmonary vascular tone in the neonate," J. Pediatr. Surg., vol. 31, pp. 137-140 (1996).
Liu and Sommer, "Restriction endonuclease fingerprinting (REF): a sensitive method for screening mutations in long, contiguous segments of DNA," Biotechniques, vol. 18, No. 3, pp. 470-477 (1995).
Liu, et al., Am J Physiol Lung Cell Mol Physiol (2006) 290:L2-L10.
Lorente et al., "Modulation of systemic hemodynamics by exogenous L-arginine in normal and bacteremic sheep," Crit. Care Med., vol. 27, pp. 2474-2479 (1999).
Lundman et al., "Mild-to-moderate hypertriglycerida in young men is associated with endothelial dysfunction and increased plasma concentrations of asymmetric dimethylarginine," J. Am. Coll. Cardiol., 38(1): 111-116 (Jul. 2001). (Abstract).
MacCallum, "Detection of PCR Amplified Products" PCR Essential Data, pp. 99-127 (1995).
Maier et al., "Activities of urea-cycle enzymes in chronic liver disease," Klin Wochenschr, vol. 57, No. 13, pp. 661-665 (Jul. 3, 1979). (Abstract).

(56) References Cited

OTHER PUBLICATIONS

Maniatis et. al., in Molecular Cloning: A Laboratory Manual, Cold Spring Harbor, N.Y., pp. 280-281 (1982).
Marrini et al., "Hepatic and renal contributions to valproic acid-induced hyperammonemia," Neurology vol. 38, pp. 365-371(1988).
Marshall et al., "Multiple organ dysfunction score: a reliable descriptor of a complex clinical outcome," Critical Care Medicine, vol. 23, pp. 1638-1652 (1995).
Matuschak and Rinaldo, "Organ interactions in the adult respiratory distress syndrome during sepsis. Role of the liver in host defense," Chest, vol. 94, pp. 400-406 (1988).
Matuschak et al., American Review of Respiratory Disease, vol. 141, pp. 1296-1306 (1990).
Matuschak,G. M., "Lung-liver interactions in sepsis and multiple organ failure syndrome," Clinics in Chest Medicine, vol. 17, pp. 83-98 (1996).
Maxwell et al., "1-arginine enhances aerobic exercise capacity in association with augmented nitric oxide production," J. Appl. Physiol., vol. 90, No. 3, pp. 933-938 (Mar. 2001). (Abstract).
Maxwell et al., "Endothelial dysfunction in hypercholesterolemia is reserved by a nutritional product designed to enhance nitric oxide activity," Cardiovasc Drugs Ther., vol. 14, No. 3, pp. 309-316 (Jun. 2000). (Abstract).
Maxwell et al., "Nutritional therapy for peripheral arterial disease: a double-blind, placebo-controlled, randomized trial of HeartBar," Vasc. Med., vol. 5, No. 1, pp. 11-19 (2000). (Abstract).
Mayo Clinic (2014) Disease and Conditions: ARDS (5 pages).
McDonald et al. (1997), J Bio Chem, 272(50):31213-31216.
McDonald et al., "Veno-occlusive disease of the liver and multiorgan failure after bone marrow transplantation: a cohort study of 355 patients," Annals of Internal Medicine, vol. 118, pp. 255-267 (1993).
MEDLINE Database Accession No. NLM7600831 [on-line], US National Library of Medicine (NLM), Bethesda, MD, US; Jul. 1995.
Meier, U., Pharm Stat (2006) 5:253-263.
Miller et al., "Effects of an acute dose of L-arginine during coronary angiography in patients with chronic renal failure: a randomized, parallel, double-blind clinical trial," Am. J. Nephrol., vol. 23, pp. 91-95 (2003).
Mitani et al., "Prolonged Administration of L-Arginine Ameliorates Chronic Pulmonary Hypertension and Pulmonary Vascular Remodeling in Rates," Circulation, vol. 96, No. 2, pp. 689-697 (1997). (Abstract).
Mitchell et al., "Syndrome of Idiopathic Hyperammonemia after High-Dose Chemotherapy: Review of Nine Cases," American Journal of Medicine, vol. 85, No. 5, pp. 662-667 (1988).
Mize et al., "Urea Cycle Disorders," Mol. Genet. Basis. Neurol. Dis., 2nd ed., pp. 1151-1174 (1997).
Mizutani et al., "Oral Administration of Arginine and Citrulline in the Treatment of Lysinuric Protein Intolerance," Tohoku J. of Exp. Med., vol. 142, pp. 15-24 (1998).
Moncada et al., "The L-Arginine-Nitric Oxide Pathway," New England Journal of Medicine, vol. 329, pp. 2002-2012 (1993).
Moorman et al., "Expression patterns of mRNAs for ammonia-metabolizing enzymes in the developing rat: the ontogenesis of hepatocyte heterogeneity," Histochemical Journal, vol. 22, pp. 457-468 (1990).
Mori et al., "Regulation of nitric oxide production by arginine metabolic enzymes," Biochem. Biophys. Res. Commun., vol. 275, No. 3, pp. 715-719 (Sep. 7, 2000). (Abstract).
Morris et al., "Hydroxyurea and arginine therapy: impact on nitric oxide production in sickle cell disease," J. Pediatr. Hematol. Oncol., vol. 25, pp. 629-634 (2003).
Morrow, "The Isoprostanes: Their Quantification as an Index of Oxidant Stress Status in Vivo," Drug Metabolism Reviews, vol. 32, Nos. 3 & 4, pp. 377-385 (2000).
Mostovoy & Ivanov (2002) "Nitric oxide in the treatment of conditions accompanied by persistent pulmonary hypertension of newborns." Internet Journal "Medical Conferences" pp. 1-4.
Mourani, et al. (2004) Am J Respiratory and Crit Care Med 170: 1006-13.
Mupanemunda, R. H., Early Human Development (1997) 47: 247-262.
Muriel, "Regulation of nitric oxide synthesis in the liver," J. Appl. Toxicol., vol. 20, No. 3, pp. 189-195 (May-Jun. 2000). (Abstract).
MX Pat Appln No. PA/a/2006/009468 (Mar. 1, 2012), Office Action, 5 pgs.
MX Pat Appln No. PA/a/2006/009468 (Jul. 6, 2011), Office Action, 4 pgs.
National Heart Lung and Blood Institute website—What is Bronchopulmonary Dysplasia [Nov. 30, 2012] (2 pages).
Needleman et al., "A general method applicable to the search for similarities in the amino acid sequence of two proteins," J. Mol. Biol., vol. 48, pp. 443-453 (1970).
Nelin et al., "L-arginine, but not D-arginine, increases nitric oxide production and vasodilates hypoxic neonatal pig lungs", FASEB Journal, vol. 18, No. 4-5, p. A327 (2004).
Nelin, et al. (2004) FASEB Journal 18(4-5): A327.
Niebauer et al., "Gene transfer of nitric oxide synthase: effects on endothelial biology," J. Am. Coll. Cardiol., vol. 34, No. 4, pp. 1201-1207 (Oct. 1999). (Abstract).
Niebauer et al., "Local L-arginine delivery after balloon angioplasty reduces monocyte binding and induces apoptosis," Circulation, vol. 100, No. 17, pp. 1830-1835 (Oct. 26, 1999). (Abstract).
Notice of Allowance corresponding to U.S. Appl. No. 09/323,472 (now U.S. Pat. No. 6,346,382) dated Aug. 9, 2001.
Notice of Allowance corresponding to U.S. Appl. No. 09/585,077 dated Oct. 8, 2003.
Notification of Transmittal of International Search Report or the Declaration corresponding to International Application No. PCT/US00/15079 dated Aug. 22, 2000.
Notification of Transmittal of the International Search Report and the Written Opinion of the International Searching Authority, or the Declaration corresponding to International Application No. PCT/US 09/32824 dated Apr. 21, 2009.
Nuzum, "Urea Cycle Enzyme Adaptation to Dietary Protein in Primates," Science, vol. 172, pp. 1042-1043 (1971).
Nyunoya et al., "Characterization and Derivation of the Gene Coding for Mitochondrial Carbamyl Phosphate Synthetase I of Rat," J. Biol. Chem., vol. 260, No. 16, pp. 9346-9356 ( Aug. 5, 1985).
O'Connor et al., "Nonalcoholic fatty liver (NASH syndrome)," Gastroenterologist, vol. 5, No. 4, pp. 316-329 (Dec. 1997). (Abstract).
Office Action corresponding to Chinese Patent Application No. 20050012693.5 dated Oct. 30, 2009.
Office Action corresponding to Chinese Patent Application No. 20050012693.5 dated May 4, 2010.
Office Action corresponding to Chinese Patent Application No. 2005800112693.5 dated Aug. 22, 2008.
Office Action corresponding to EP Patent Application Serial No. 05723789 dated Mar. 31, 2011.
Office Action corresponding to European Patent Application No. 06 005 642.1-2403 dated Jul. 25, 2011.
Office Action corresponding to European Patent Application No. 06 005 642.1-2403 dated Nov. 12, 2010.
Office Action corresponding to European Patent Application Serial No. 06 005 642.1-2403 dated Jul. 25, 2011.
Office Action corresponding to Israeli Patent Application No. 177224 dated Apr. 26, 2011.
Office Action corresponding to Mexican Patent Application No. PA/a/2006/009468 dated May 12, 2011.
Office Action corresponding to U.S. Appl. No. 10/785,374 dated Sep. 27, 2011.
Office Action corresponding to U.S. Appl. No. 09/989,956 dated Oct. 18, 2006.
Office Action corresponding to U.S. Appl. No. 09/989,956 dated Jan. 30, 2006.
Office Action corresponding to U.S. Appl. No. 09/989,956 dated Jul. 1, 2004.
Office Action corresponding to U.S. Appl. No. 09/323,472 (now U.S. Pat. No. 6,346,382) dated Dec. 20, 2000.

(56) References Cited

OTHER PUBLICATIONS

Office Action corresponding to U.S. Appl. No. 09/585,077 dated Jul. 3, 2002.
Office Action corresponding to U.S. Appl. No. 12/322,434 dated Apr. 5, 2011.
Office Action corresponding to U.S. Appl. No. 12/364,078 dated Oct. 21, 2010.
Office Action corresponding to U.S. Appl. No. 12/364,078 dated Mar. 4, 2010.
Office Action corresponding to U.S. Appl. No. 12/122,117 dated Apr. 21, 2010.
Office Action corresponding to U.S. Appl. No. 12/122,117 dated Jul. 22, 2010.
Office Action corresponding to U.S. Appl. No. 12/122,117 dated Mar. 23, 2011.
Office Action corresponding to U.S. Appl. No. 10/785,374 dated Sep. 14, 2007.
Office Action corresponding to U.S. Appl. No. 10/785,374 dated Jul. 25, 2008.
Office Action corresponding to U.S. Appl. No. 10/785,374 dated Mar. 2, 2010.
Olsvik et al., "A nested PCR followed by magnetic separation of amplified fragments for detection of Escherichia coli Shigalike toxin genes," Molecular and Cellular Probes, vol. 5, pp. 429-435 (Dec. 1991).
Palmer et al., "L-Arginine is the Physiological Precursor for the Formation of Nitric Oxide in Endothelium-Dependent Relaxation," Biochem. Biophys. Res. Commun., vol. 153, pp. 1251-1256 (1988).
Paulus et al., "Myocardial contractile effects of L-arginine in the human allograft," J. Am. Coll. Cardiol., vol. 29, pp. 1332-1338 (1997).
PCT IPRP (dated Sep. 8, 2006), PCT/US05/06081, 17 pgs.
Pearson et al., "Neonatal Pulmonary Hypertension—Urea-Cycle Intermediates, Nitric Oxide Production, and Carbamoyl-Phosphate Synthetase Function," N. Engl. J. Med., vol. 344, No. 24, pp. 1832-1838 (Jun. 12, 2001).
Pernow et al., "L-Arginine Protects from Ischemia-Reperfusion-Induced Endothelial Dysfunction in Humans In Vivo," J. Appl. Physiol., vol. 95, pp. 2218-2222 (2003). (Abstract).
Perrone et al. (2012), J Clin Neonat, 1(3):109-114.
"Persistierende fetale Zirkulation (PFC-Syndrom)" (2009).
Pierson, D.L., "A rapid colorimetric assay for carbamyl phosphate synthetase I," J. Biochem. Biophys. Methods, vol. 3, pp. 31-37 (1980).
Price et al., "Prognostic Indicators for Blood and Marrow Transplant Patients Admitted to an Intensive Care Unit," American Journal of Respiratory & Critical Care Medicine, vol. 158, pp. 876-884 (1998).
Pulmonary Hypertension—PubMed Health website A.D.A.M. Medical Encyclopedia (2011) [Nov. 30, 2012] (5 pages).
Rabier et al., "Effects of organic acids on the synthesis of citrulline by intact rat liver mitochondria," Biochimie, vol. 68, pp. 639-647 (1986).
Rabier et al., "Propionate and succinate effects on acetyl glutamate biosynthesis by rat liver mitochondria," Biochem. & Biophys. Research Comm., vol. 91, pp. 456-460 (1979).
Rabinstein et al., "Patterns of Cerebral Infarction in Aneurysmal Subarachnoid Hemorrhage," Stroke, vol. 36, pp. 992-997 (2005).
Raiha and Suihkonen, J. Acta Paediatrica Scand., vol. 57, pp. 121-127 (1968).
Ravnik et al., "Long-term Cognitive Deficits in Patients with Good Outcomes after Aneurysmal Subarachnoid Hemorrhage from Anterior Communicating Artery," Croat. Med. J., vol. 47, pp. 253-263 (2006).
Richardson et al., "Prevention and treatment of hepatic venocclusive disease after high-dose cytoreductive therapy," Leukemia & Lymphoma, vol. 31, pp. 267-277 (1998).
Rinaldo et al., "Nitric oxide inactivates xanthine dehydrogenase and xanthine oxidase in interferon-gamma-stimulated macrophages," American Journal of Respiratory Cell & Molecular Biology, vol. 11, pp. 625-630 (1994).
Roberts, J. D., et al., "Inhaled nitric oxide in persistent pulmonary hypertension of the newborn," Lancet, vol. 340, pp. 818-819 (1992).
Roblek et al. (May 2010), PLoS ONE, 5(5):e10604.
Rodriguez-Aparicio, L. B. et al., Biochemistry, vol. 28, pp. 3070-3074 (1989).
Romero et al., "Therapeutic use of citrulline in cardiovascular disease," Cardiovasc.Drug Rev., vol. 24, pp. 275-290 (2006).
Romero, et al. (2006) Cardiovascular Drug Reviews 24(3-4): 275-290.
Rubenfeld et al., "Withdrawing life support from mechanically ventilated recipients of bone marrow transplants: a case for evidence-based guidelines," Annals of Internal Medicine, vol. 125, pp. 625-633 (1996).
Ruberti, et al. (1969) "Hepatoprotective Effect Association Amino Acids the Krebs-Henseleit Cycle—Clinical and Statistical Consideration" 50(5): 397-425.
Rubio and Grisolia, "Human Carbamoylphosphate Synthetase I," Enzyme, vol. 26, pp. 233-239 (1981).
Rubio, V., (Review) Biochemical Society Transactions, vol. 21, pp. 198-202 (1993).
Ruiz & Tejerina (1998) British Journal of Pharmacology 125: 186-192.
Russell, et al. (1998) Anesth Analg 87:46-51.
Ryan, R. M., "A new look at bronchopulmonary dysplasia classification," J. Perinatology, vol. 26, pp. 207-209 (2006).
Saijyo et al. "Autonomic Nervous System Activity During Infusion of L-Arginine in Patients with Liver Cirrhosis," Liver, vol. 18, No. 1, pp. 27-31 (1998). (Abstract).
Saiki et al., "A Novel Method for the Detection of Polymorphic Restriction Sites by Cleavage of Oligonucleotide Probes: Application to Sickle-Cell Anemia," Bio/Technology, vol. 3, pp. 1008-1012 (1985).
Saiki, R.K., "Amplification of Genomic DNA," Chapter 2 in PCR Protocols: A Guide to Methods and Applications, Innis, M.A. et al, eds., Academic Press, Inc., San Diego, pp. 13-21 (1990).
Sakowtiz et al., "Relation of Cerebral Energy Metabolism and Extracellular Nitrite and Nitrate Concentrations in Patients after Aneurysmal Subarachnoid Hemorrhage," Journal of Cerebral Blood Flow and Metabolism, vol. 21, pp. 1067-1076 (2001).
Sallaam (2013) Persistent Newborn Pulmonary Hypertension Medscape (7 pages).
Saugstad (2003) Semin Neonatol. 8(1): 39-49 [Abstract].
Schmid, R. D., Clin. Chim. Acta., vol. 74, pp. 39-42 (1977).
Schreiber et al. "Inhaled nitric oxide in premature infants with respiratory distress syndrome", New England J. Med., vol. 349, pp. 2099-2107 (2003).
Schulman et al., "L-arginine therapy in acute myocardial infarction: the Vascular Interaction With Age in Myocardial Infarction (VINTAGE MI) randomized clinical trial," JAMA, vol. 295, pp. 58-64 (Jan. 4, 2006).
Schulze-Neick, et al. (1998) Pediatric Anesthesia 87: 46-51.
Schulze-Neick, et al. (1999) Circulation 100:749-755.
Schwartz & Dayhoff (1978) Matrices for Detecting Distant Relationships, Atlas of Protein Sequence and Structure, National Biomed Res Foundation, 5(supp 3): 353-358.
Schwarzacher et al. "Effects of stenting on adjacent vascular distensibility and neointima formation: role of nitric oxide," Vasc. Med., vol. 6, No. 3, pp. 139-144 (2001).
Schwarzacher et al., "Local intramural delivery of L-arginine enhances nitric oxide generation and inhibits lesion formation after balloon angioplasty," Circulation, vol. 95, No. 7, pp. 1863-1869 (Apr. 1, 1997). (Abstract).
Sercombe et al., "Cerebrovascular Inflammation Following Subarachnoid Hemorrhage," Jpn. J. Pharmacol., vol. 88, pp. 227-249 (2002).
SG 201005570-5 (Oct. 27, 2011), Search Rpt, 15 pgs.
Shigesada et al., Journal of Biological Chemistry, vol. 246, pp. 5588-5595 (1971).
Shimoda L., et al., Physiol Res (2000) 49:549-560.

(56) References Cited

OTHER PUBLICATIONS

Shore, et al. The Journal of Biological Chemistry 254(9): 3141-3144.
Shulman et al., "Veno-occlusive disease of the liver after marrow transplantation: histological correlates of clinical signs and symptoms," Hepatology, vol. 19, pp. 1171-1181 (1994).
Simko et al., "L-arginine fails to protect against myocardial remodelling in L-NAME-induced hypertension," Eur. J. Clin. Invest, vol. 35, pp. 362-368 (2005).
Singh et al., "Nutritional Management of Urea Cycle Disorders," Crit. Care Clin., vol. 21, pp. S27-S35, (2005).
Smith et al., "Comparisons of biosequences," Adv. Appl. Math., vol. 2, pp. 482-489 (1981).
Smith et al., "Nitric oxide precursors and congenital heart surgery: A randomized controlled trial of oral citrulline," The Journal of Thoracic and Cardiovascular Surgery, vol. 132, No. 1, pp. 58-65 (Jul. 2006).
Smith et al., "Urea Cycle Disorders: Clinical Presentation Outside the Newborn Period," Crit Care Clin, vol. 21, pp. S9-S17 (2005).
Smith, et al. (2006) Journal of Thoracic and Cardiovascular Surgery 132(1): 58-65.
Stamler et al. (1992), Sci, 258(5090):1898-1902.
Stanker et al. (Jun. 1, 1986), Jimmunol, 136(11):4174-4180.
Stapleton et al., "Comparison of the Functional Differences for the Homologous Residues Within the Carboxy Phosphate and Carbamate Domains of Carbamoyl Phosphate Synthetase," Biochemistry vol. 35, pp. 14352-14361.
Stier et al., "Dietary arginine fails to protect against cerebrovascular damage in stroke-prone hypertensive rats," Brain Res., vol. 549, pp. 354-356 (May 24, 1991).
Stuhlinger et al., "Homocysteine impairs the nitric oxide synthase pathway: role of asymmetric dimethylarginine," Circulation, vol. 104, No. 21, pp. 2569-2575 (Nov. 20, 2001). (Abstract).
Stuhlinger et al., "Relationship between insulin resistance and an endogenous nitric oxide synthase inhibitor," JAMA, 287, No. 11, pp. 1420-1426 (Mar. 20, 2002). (Abstract).
Subhedar, N. V., Acta Paediatr suppl (2004) 444:29-32.
Summar and Tuchman, "Proceedings of a Consensus Conference for the Management of Patients with Urea Cycle Disorders," J. Pediatr., vol. 138, pp. S6-S10 (2001).
Summar et al., Mol. Genet. Metab. (2004) 81 Suppl 1: S12-9.
Summar ML, et al., "Physical and linkage mapping of human carbamyl phosphate synthetase I (CPS1) and reassignment from 2p to 2q35," Cytogenetics & Cell Genetics, vol. 71, pp. 266-267 (1995).
Summar, M. L., "Molecular genetic research into carbamoyl-phosphate synthase I: molecular defects and linkage markers," Journal of Inherited Metabolic Disease, vol. 21, Sqppl. 1, pp. 30-39 (1998).
Summar, M., "Current strategies for the management of neonatal urea cycle disorders," J. Pediatr., vol. 138, pp. S30-S39 (2001).
Surdacki et al. Wien Klin Wochenschr. (1994) 106(16): 521-6.
Surdacki et al., "Lack of beneficial effects of L-arginine infusion in primary pulmonary hypertension," Wien. Klin. Wochenschr., vol. 106, pp. 521-526 (1994).
Suschek, et al. 2003, Circulation, 107(20):2607-2614.
Suzuki et al., "Effect of Local Delivery of L-Arginine on In-stent Restenosis in Humans," The American Journal of Cardiology, vol. 89, pp. 363-367 (Feb. 15, 2002).
Takiguchi, "Transcriptional regulation of genes for ornithine cycle enzymes," Biochem J., vol. 312, pp. 649-659 (1995).
Thorell et al., "Optical Coherence Tomography: A New Method to Assess Aneurysm Healing," J. Neurosurg., vol. 102, No. 2, pp. 348-354 (2005).
Toh et al., European Journal of Biochemistry, vol. 215, pp. 687-696 (1993).
Treem et al., "Disorders of the mitochondria," Semin. Liver Dis., vol. 18, No. 3, pp. 237-253 (1998). (Abstract).
Tse et al., "Hyperammonemia following allogeneic bone marrow transplantation," American Journal of Hematology, No. 38, pp. 140-141 (1991).
Turley, J. E. et al., Am J Physiol Lung Cell Mol Physiol (2008) 284:L489-L500.
Uemura et al., "Rapid and efficient vascular transport of arginine polymers inhibits myointimal hyperplasia," vol. 102, No. 21, pp. 2629-2635 (Nov. 21, 2000). (Abstract).
U.S. Appl. No. 10/785,374 (Apr. 2, 2012), Interview Summary, 2 pgs.
U.S. Appl. No. 12/122,117 (Jan. 25, 2012), Notice of Allowance, 7 pgs.
U.S. Appl. No. 12/122,117 (Nov. 10, 2011), Advisory Action, 3 pgs.
U.S. Appl. No. 12/122,117 (Nov. 25, 2011), Interview Summary, 3 pgs.
U.S. Appl. No. 12/364,078 (May 23, 2011), Advisory Action.
Vadivel et al. (2010), Pediatr Res, 68(6):519-525.
Van den Hoff et al. "Evolutionary relationships of the carbamoylphosphate synthetase genes," Journal of Molecular Evolution, vol. 41, pp. 813-832 (1995).
Van der Schaaf et al., "New Detected Aneurysms on Follow-Up Screening in Patients with Previously Clipped Intracranial Aneurysms: Comparison with DSA or CTA at the Time of SAH," Stroke, vol. 36, pp. 1753-1758 (2005).
Vassal et al., "Busulfan disposition and hepatic veno-occlusive disease in children undergoing bone marrow transplantation", Cancer Chemo. Phar., vol. 37, pp. 247-253 (1996).
Vinten-Johansen et al. (1995), Int. J Cardiology, 50:273-281.
Vosatka et al., "Arginine Deficiency Accompanies Persistent Pulmonary Hypertension of the Newborn," Biol. Neonate, vol. 66,. pp. 65-70 (1994).
Vosatka, "Persistent pulmonary hypertension of the newborn," N Engl J Med, vol. 346, No. 11, p. 864 (Mar. 14, 2002).
Ware, et al. (2013) Critical Care 17: R10.
Warter et al., Revue Neurologique, vol. 139, pp. 753-757 (1983).
Waugh et al. "Oral citrulline as arginine precursor may be beneficial in sickle cell disease: early phase two results," J. Natl. Med. Assoc., vol. 93, No. 10, pp. 363-371 (Oct. 2001). (Abstract).
Wetmur & Davidson, J. Mol. Biol., vol. 31, pp. 349-370 (1968).
Wilson et al., "L-arginine supplementation in peripheral arterial disease: no benefit and possible harm," Circulation, vol. 116, pp. 188-195 (Jul. 10, 2007).
Wingard et al., Bone Marrow Transplantation, vol. 4, pp. 685-689 (1989).
Wong et al., "Use of Phenytoin and Other Anticonvulsant Prophylaxis in Patients with Aneurysmal Subarachnoid Hemorrhage Response," Stroke, vol. 36, p. 2532 (2005).
Zamora et al., "Plasma L-arginine concentration, oxygenation index, and systemic blood pressure in premature infants," Crit. Care Med., vol. 26, pp. 1271-1276 (1998).

\* cited by examiner

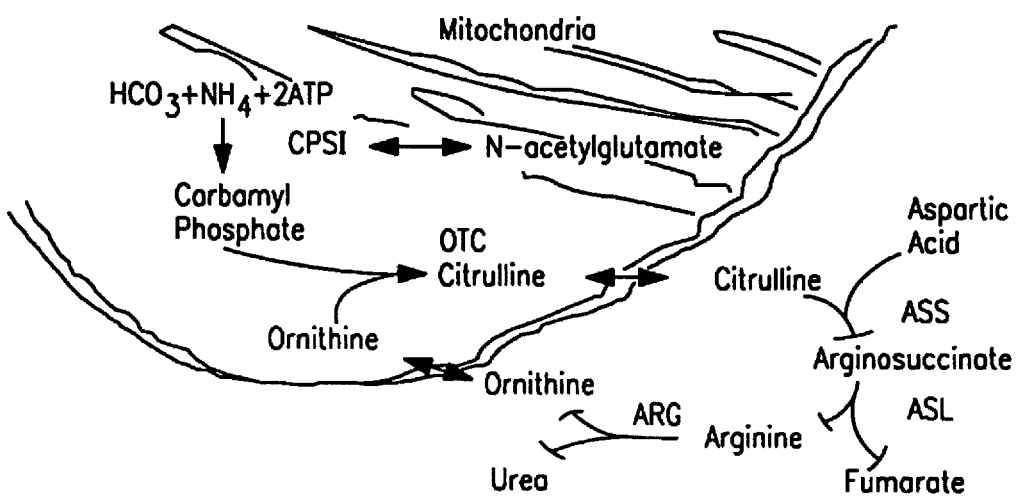

METHODS AND COMPOSITIONS FOR TREATMENT FOR CORONARY AND ARTERIAL ANEURYSMAL SUBARACHNOID HEMORRHAGE

RELATED APPLICATION INFORMATION

This patent application is a divisional patent application of U.S. patent application Ser. No. 13/331,678, filed Dec. 20, 2011, now U.S. Pat. No. 9,943,494, which is a continuation of U.S. patent application Ser. No. 12/322,434, filed Feb. 2, 2009, now abandoned, which claims priority to U.S. Provisional Patent Application No. 61/025,170, filed Jan. 31, 2008, the entire contents of these patent applications are herein incorporated by reference.

TECHNICAL FIELD

The presently disclosed subject matter relates to the treatment of Aneurysmal Subarachnoid Hemorrhage (SAH), complications associated with SAH (including vasospasm), and vasospasm associated with atheroscelerosis, including but not limited to that associated with coronary arterial disease.

BACKGROUND

Aneurysmal Subarachnoid Hemorrhage (SAH) is one of the leading causes of morbidity and mortality associated with stroke worldwide. SAH is a neurological emergency characterized by extravasations of blood into spaces covering the central nervous system that are filled with cerebrospinal fluid. Several complications such as hydrocephalus, rebleeding, cerebral vasospasm, seizures, myocardial injury, and pulmonary edema can result from SAH.

SAH is a major concern throughout the world, with varying incidences of between about 1 and 96 incidents per 100,000 person/year (Batista da Costa Jr. et al. (2004) *Arq Neuro-Psiquiatr* (Sao Paulo) 62:245-249), with a worldwide incidence of about 10 per 100,000 person/year (Batista da Costa Jr. et al. (2004) *Arq Neuro-Psiquiatr* (Sao Paulo) 62:245-249). According to Suarez et al., SAH affects 21,000-33,000 people per year in the United States, and represents about 2-5% of all new strokes (Suarez et al. (2006) *N Engl J Med* 354:387-396). About 80% of cases of SAH result from rupture of an intracranial aneurysm, which itself is associated with significant risk of complications, including death. The peak age of incidence is 55-60 years, and about 20% occurs between the ages of 15 and 45 years. There is a gender difference in SAH, with a female preponderance characterized by a ratio of female to male patients ranging from 1.6-4.16:1. The incidence of SAH is also higher in African-Americans than in Caucasians.

Recent statistics indicate that about 30% of SAH patients die within the first 24 hours, and another 25-30% die within the following 4 weeks (Flett et al. (2005) *AJNR Am J Neuroradiol* 126:367-372). Besides the initial risks associated with SAH, a significant percentage of patients who have suffered SAH suffer from long-term cognitive impairment (Suarez et al. (2006) *N Engl J Med* 354:387-396), and thus SAH is associated with substantial impacts on health care resources.

While symptom management plays a major role in the treatment of SAH, there continues to be a long felt need for treatment strategies that address the underlying physiological bases for the development of secondary complications of SAH.

SUMMARY

The presently disclosed subject matter provides methods and compositions for treating SAH and/or associated complications in a subject. In some embodiments, an effective amount of a nitric oxide precursor is administered to a subject suffering from SAH and/or associated complications and/or at risk for suffering complications associated with SAH (e.g., vasospasm). In some embodiments, the nitric oxide precursor comprises at least one of citrulline, a precursor that generates citrulline in vivo, a pharmaceutically acceptable salt thereof, and combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm.

The presently disclosed subject matter also provides methods and compositions for treating vasospasm. In some embodiments, the subject to be treated suffers from vasospasm associated with SAH. In some embodiments, the subject to be treated has suffered trauma that results in vasospasm (e.g., trauma that results in SAH). The methods can comprise administering to a subject in need thereof an effective amount of a nitric oxide precursor. In some embodiments, the nitric oxide precursor comprises at least one of citrulline, a precursor that generates citrulline in vivo, a pharmaceutically acceptable salt thereof, and combinations thereof. In some embodiments, the subject to be treated is suffering from vasospasm associated with SAH. In some embodiments, the nitric oxide precursor, such as citrulline, is administered orally. In some embodiments, the nitric oxide precursor, such as citrulline, is administered intravenously.

It is therefore an object of the presently disclosed subject matter to provide for treatment for SAH, vasospasm, and/or associated complications in a subject.

An object of the presently disclosed subject matter having been stated hereinabove, other objects will become evident as the description proceeds, when taken in connection with the accompanying drawings and examples as best described hereinbelow.

BRIEF DESCRIPTION OF THE DRAWINGS

FIG. 1 is a schematic of the urea cycle.

DETAILED DESCRIPTION

A considerable number of people worldwide are afflicted with Aneurysmal Subarachnoid Hemorrhage (SAH). The mortality rate for this condition is quite high, and even patients who survive SAH frequently experience dramatic reductions in their qualities of life. Current therapies in use can often prevent the death of a person who has experienced SAH if begun within an appropriate timeframe, but even successfully preventing that patient's death does not address the development of serious secondary complications. Therapies aimed at preventing secondary complications such as vasospasm and its sequelae, for example, are provided in accordance with aspects of the presently disclosed subject matter.

I. General Considerations

The in vivo synthetic pathway for arginine commences with ornithine. Ornithine is combined with carbamyl phosphate to produce citrulline, which in turn is combined with aspartate, in the presence of adenosine triphosphate (ATP), to produce argininosuccinate. In the final step, fumarate is split from argininosuccinate, to produce arginine. The degradative pathway for arginine is by the hydrolytic action of arginase, to produce ornithine and urea. These reactions form the urea cycle. The urea cycle serves as the primary pathway for removing waste nitrogen produced by the metabolism of endogenous and exogenous proteins, and is shown schematically in FIG. 1. In addition to its role in nitrogen clearance, the urea cycle is the body's intrinsic source of arginine which acts as a precursor of nitric oxide (NO), a potent vasodilator.

SAH typically results from rupture of a cranial aneurysm which results in leakage of blood into compartments of the nervous system that contain cerebrospinal fluid. Primary symptomology typically includes sudden onset of headache, which is usually very severe, nausea, vomiting, neck pain, photophobia, and loss of consciousness (Suarez et al. (2006) *N Engl J Med* 354:387-396), which is frequently associated with neurological deficits that become apparent on physical exam (Suarez et al. (2006) *N Engl J Med* 354:387-396). Hydrocephalus (20%), rebleeding (7%), cerebral vasospasm (46%), seizures (30%), hyponatremia (28%), myocardial injury (35%), and pulmonary edema (23%) occur in a significant percentage of patients, even if the damage to the underlying vessel(s) is repaired. These events also frequently lead to additional secondary complications, including seizures, pulmonary edema, cardiac arrhythmias, electrolyte, disturbances, and neuropsychological complications such as problems with memory, mood, and neuropsychological function.

While the causes of the various sequelae of SAH are multifactorial, certain observations have been made. For example, decreased availability of nitric oxide in cerebral vessels has been observed, as has increased synthesis of endothelin or increase sensitivity of the arteries to this factor. Alterations in smooth muscle cells that promote a contracted state and activation of signal transduction mechanisms that can alter calcium sensitivity have also been reported. Additionally, increased thrombogenicity of the endothelium and/or platelet adhesion contributing to arterial dysfunction can occur, as can disruption of the blood brain barrier, inflammation, vasoconstriction, and injury to cerebral vessels of all sizes.

Given its devastating impact on patients, rapid diagnosis and treatment of SAH is critical. Typically, patients presenting with symptoms suggestive of SAH are subjected to head CT, which can detect the presence of SAH. If a subarachnoid hemorrhage is detected, FT angiography and/or cerebral angiography can locate an aneurysm, which is then repaired. If, however, the angiography is normal, CT angiography is typically repeated 1-3 weeks subsequent to initial presentation, optionally followed by brain, brain stem, and/or spinal cord imaging. In those cases where heat CT does not detect a subarachnoid hemorrhage, testing of cerebrospinal fluid obtained by lumbar puncture can also provide indicators of SAH, which then can be confirmed by angiography.

Once SAH is diagnosed, treatment generally includes securing of the aneurysm by neurosurgical clipping or endovascular coiling. Treatment of associated symptoms including, but not limited to hypertension, hyperthermia, hyperglycemia, and ischemia are performed as needed. Given that complications associated with SAH typically develop over the course of several weeks, a subject generally remains hospitalized for extended periods in order to provide continuous monitoring of the subject's condition.

II. Therapeutic Methods

The presently disclosed subject matter provides methods for treating SAH and/or associated complications in a subject. In some embodiments, an effective amount of a nitric oxide precursor is administered to a subject suffering from SAH and/or associated complications and/or at risk for suffering complications associated with SAH. Representative examples of such complications are disclosed herein above.

In some embodiments, the nitric oxide precursor comprises at least one of citrulline, a precursor that generates citrulline in vivo, a pharmaceutically acceptable salt thereof, and combinations thereof. See FIG. 1. In some embodiments, the nitric oxide precursor is selected from the group including, but not limited to, citrulline, arginine, or combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm. Representative examples of such conditions are disclosed herein above.

In some embodiments, the subject suffering from a complication, such as vasospasm, suffers from relative hypocitrullinemia. The term "relative hypocitrullinemia" refers to a state in which the subject suffering from a complication has reduced plasma citrulline as compared to a subject not suffering from a complication.

In some embodiments, the subject suffers from hypocitrullinemia. In some embodiments the hypocitrullinemia is characterized by plasma citrulline levels of 37 µmol/liter, in some embodiments, ≤25 µmol/liter, in some embodiments, ≤20 µmol/liter, in some embodiments, ≤10 µmol/liter, in some embodiments, ≤5 µmol/liter.

The presently disclosed subject matter also provides methods and compositions for treating vasospasm. In some embodiments, the subject to be treated suffers from vasospasm associated with SAH. In some embodiments, the subject to be treated has suffered trauma that results in vasospasm (e.g., trauma that results in SAH). In some embodiments the vasospasm is associated with atherosclerosis in the subject. In some embodiments the atherosclerosis is associated with coronary artery disease in the subject, with carotid arterial disease in the subject, with peripheral arterial disease in the subject, and combinations thereof.

In some embodiments, the nitric oxide precursor comprises at least one of citrulline, a precursor that generates citrulline in vivo, a pharmaceutically acceptable salt thereof, and combinations thereof. See FIG. 1. In some embodiments, the nitric oxide precursor is selected from the group including, but not limited to, citrulline, arginine, or combinations thereof. In some embodiments, the nitric oxide precursor, such as citrulline, is administered orally. In some embodiments, the nitric oxide precursor, such as citrulline, is administered intravenously. In some embodiments, the subject to be treated is a subject suffering from vasospasm. In some embodiments, the subject to be treated is a subject suffering from an acute condition associated with vasospasm (e.g. ischemia and/or angina in coronary arterial disease).

In some embodiments, the subject suffering from a complication, such as vasospasm, suffers from relative hypocitrullinemia. The term "relative hypocitrullinemia" refers to a state in which the subject suffering from a complication has reduced plasma citrulline as compared to a subject not suffering from a complication.

As used herein, the phrase "treating" refers to both intervention designed to ameliorate a condition in a subject (e.g., after initiation of a disease process or after an injury) as well as to interventions that are designed to prevent the condition from occurring in the subject. Stated another way, the terms "treating" and grammatical variants thereof are intended to be interpreted broadly to encompass meanings that refer to reducing the severity of and/or to curing a condition, as well as meanings that refer to prophylaxis. In this latter respect, "treating" can refer to "preventing" to any degree, or otherwise enhancing the ability of the subject to resist the process of the condition, such as a subject at risk to suffer the condition.

The subject treated in the presently disclosed subject matter in its many embodiments is desirably a human subject, although it is to be understood that the principles of the presently disclosed subject matter indicate that the presently disclosed subject matter is effective with respect to all vertebrate species, including warm-blooded vertebrates such as mammals and birds, which are intended to be included in the term "subject". In this context, a mammal is understood to include any mammalian species in which treatment is desirable, such as but not limited to agricultural and domestic mammalian species.

Thus, provided is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, provided is the treatment of livestock, including, but not limited to, domesticated swine (pigs and hogs), ruminants, horses, poultry, and the like.

III. Pharmaceutical Compositions

An effective dose of a composition of the presently disclosed subject matter is administered to a subject in need thereof. An "effective amount" is an amount of a composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. By way of example and not limitation, doses of compositions can be started at levels lower than required to achieve the desired therapeutic effect and to gradually increase the dosage until the desired effect is achieved. The potency of a composition can vary, and therefore an "effective amount" can vary.

After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, gender, severity and stage of symptoms, and the presence of additional deleterious physical conditions.

By way of additional examples, the amount of active ingredient that may be combined with the carrier materials to produce a single dosage form will vary depending upon the subject to be treated and the particular mode of administration. For example, a formulation intended for administration to humans can contain from 0.5 mg to 5 g of active agent compounded with an appropriate and convenient amount of carrier material which may vary from about 5 to about 95 percent of the total composition. For example, in a human adult, the doses per person per administration are generally between 1 mg and 500 mg up to several times per day. Thus, dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

The nitric oxide precursor is administered in some embodiments in a dose ranging from about 0.01 mg to about 1,000 mg, in some embodiments in a dose ranging from about 0.5 mg to about 500 mg, and in some embodiments in a dose ranging from about 1.0 mg to about 250 mg. The nitric oxide precursor can also be administered in some embodiments in a dose ranging from about 100 mg to about 30,000 mg, and in some embodiments in a dose ranging from about 250 mg to about 1,000 mg. A representative dose is 3.8 g/m2/day of arginine or citrulline (molar equivalents, MW L-citrulline 175.2, MW L-arginine 174.2).

Representative intravenous citrulline solutions can comprise a 100 mg/ml (10%) solution. Representative intravenous citrulline dosages can comprise 200 mg/kg, 400 mg/kg, 600 mg/kg, and 800 mg/kg. In some embodiments, for example but not limited to a 600 or 800 mg/kg dosage, the dose can be decreased by an amount ranging from 50 mg/kg and 100 mg/kg to mitigate observed undesired effects on systemic blood pressure. In some embodiments, doses can be administered one or more times during a given period of time, such as a day.

In some embodiments a pharmaceutical composition comprises an amount of citrulline effective to raise plasma citrulline level to treat a complication as disclosed herein in a subject. In some embodiments, the level is determined by comparing plasma citrulline levels in a subject to be treated to that observed in a subject not suffering from the complication. In some embodiments, the amount of citrulline is effective to raise plasma citrulline level in a subject to at least 5 µmol/liter, optionally at least 10 µmol/liter, optionally at least 20 µmol/liter, optionally at least 25 µmol/liter, and optionally about 37 µmol/liter.

In some embodiments, the presently disclosed subject matter provides pharmaceutical compositions comprising a nitric oxide precursor and a pharmaceutically acceptable carrier, such as a pharmaceutically acceptable carrier in humans. In some embodiments, the presently disclosed subject matter provides pharmaceutical compositions comprising citrulline or arginine in dosages as described above.

A composition of the presently disclosed subject matter is typically administered orally or parenterally in dosage unit formulations containing standard nontoxic pharmaceutically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic acceptable diluent or solvent, for example, as a solution in 1,3-butanediol.

Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Exemplary carriers include neutral saline solutions buffered with phosphate, lactate, Tris, and the like.

In a representative embodiment doses can be administered to a subject several times during a relevant treatment period, including but not limited to 1, 2, 3, 4, 5, 6 or more dosages.

It will be understood, however, that the specific dose level for any particular subject will depend upon a variety of factors including the age, body weight, general health, sex, diet, time of administration, route of administration, rate of excretion, drug combination and the severity of the particular disease undergoing therapy.

EXAMPLES

The following Examples have been included to illustrate representative modes of the presently disclosed subject matter. In light of the present disclosure and the general level of skill in the art, those of skill will appreciate that the following Examples are intended to be exemplary only in that numerous changes, modification, and alterations can be employed without departing from the spirit and scope of the presently disclosed subject matter.

Overview of Examples

While symptom management plays a major role in the treatment of SAH, there continues to be a long felt need for treatment strategies that address the underlying physiological bases for the development of secondary complications of SAH. For example, one of the key pathological mechanisms following aneurismal SAH is decreased availability of nitric oxide in cerebral vessels resulting in contraction of smooth muscles or vasospasm. By comparing plasma from patients with and without vasospasm it has been determined by the instant co-inventors there is a significant difference in citrulline levels such that patients with vasospasm have lower levels of citrulline as compared to patients without vasospasm. While it is not desired to be bound by any particular theory of operation, these results suggest that citrulline acting as a NO precursor can be a treatment for both SAH and coronary arterial disease through a similar mechanism of supporting vascular relaxation through restoring an adequate supply of citrulline which can act as a nitric oxide precursor amongst other actions.

Examples 1 and 2 present the results of assaying plasma levels of citrulline, ornithine, arginine, and nitric oxide in subjects with and without vasospasm. The samples were separated by 24 hours in time from collection. In Example 1, levels were assayed after early collection, and in Example 2, levels were assayed after late collection.

Example 1

COMPARISON OF PLASMA (EARLY COLLECTION) IN PATIENTS WITHOUT AND WITH VASOSPASM

| Parameter | Without vasospasm[1] | With vasospasm[1] | p-value |
|---|---|---|---|
| Citrulline (nM/ml) | 9.12 ± 1.2 | 5.66 ± 1.2 | 0.08 |
| Ornithine (nM/ml) | 31.66 ± 5.7 | 16.46 ± 3.4 | 0.04 |
| Arginine (nM/ml) | 34.88 ± 9.7 | 22.54 ± 4.3 | 0.14 |
| Nitric Oxide (µM) | 27.36 ± 4.8 | 30.72 ± 9.6 | 0.38 |

[1]n = 5; data expressed as mean ± standard error

Example 2

COMPARISON OF PLASMA (LATE COLLECTION) IN PATIENTS WITHOUT AND WITH VASOSPASM

| Parameter | Without vasospasm | With vasospasm[1] | p-value |
|---|---|---|---|
| Citrulline (nM/ml) | 8.62 ± 1.2 | 4.81 ± 1.6 | 0.12 |
| Ornithine (nM/ml) | 42.60 ± 4.9 | 25.22 ± 6.5 | 0.06 |
| Arginine (nM/ml) | 47.76 ± 16 | 26.52 ± 9.0 | 0.14 |
| Nitric Oxide (µM) | 58.85 ± 39 | 48.01 ± 30 | 0.41 |

[1]n = 5; data expressed as mean ± standard error

REFERENCES

The references listed below as well as all references cited in the specification are incorporated herein by reference to the extent that they supplement, explain, provide a background for or teach methodology, techniques and/or compositions employed herein.

Batista da Costa Jr. et al. (2004) *Arq Neuro-Psiquiatr* (Sao Paulo) 62:245-249.
Suarez et al. (2006) *N Engl J Med* 354:387-396.
Flett et al. (2005) *AJNR Am J Neuroradiol* 26:367-372.
Published U.S. Patent Application Number US-2004-0235953-A1, published Nov. 25, 2004.
PCT International Patent Application Publication No. WO 2005/082042, published Sep. 9, 2005.
U.S. Pat. No. 6,343,382.
U.S. Pat. No. 6,743,823.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating a complication associated with aneurysmal subarachnoid hemorrhage (SAH) in a subject having SAH and relative hypocitrullinemia, wherein the complication is cerebral vasospasm, said method comprising intravenously administering to the subject suffering from SAH and relative hypocitrullinemia an effective amount of citrulline, a pharmaceutically acceptable salt thereof, or combinations thereof, said amount being effective to raise the subject's plasma citrulline level to at least 20 µmol/liter, whereby the effective amount of citrulline, the pharmaceutically acceptable salt thereof, or combinations thereof is enough to ensure the subject is not suffering from relative hypocitrullinemia.

2. The method of claim 1, wherein the subject has suffered trauma that results in aneurysmal subarachnoid hemorrhage (SAH).

3. The method of claim 1, wherein the citrulline, a pharmaceutically acceptable salt thereof, or a combination thereof is administered in a dose ranging from about 100 mg to about 30,000 mg.

4. The method of claim 3, wherein the citrulline, a pharmaceutically acceptable salt thereof, or a combination thereof is administered in a dose ranging from about 250 mg to about 1,000 mg.

5. The method of claim 1, wherein the amount of citrulline is effective to raise the subject's plasma citrulline to at least 25 µmol/liter.

6. The method of claim 1, wherein the amount of citrulline is effective to raise the subject's plasma citrulline to at least about 37 µmol/liter.

\* \* \* \* \*